(12) United States Patent
Viola

(10) Patent No.: US 8,006,888 B2
(45) Date of Patent: Aug. 30, 2011

(54) MULTIPLE COIL STAPLE AND STAPLE APPLIER

(75) Inventor: Frank J. Viola, Sandy Hook, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/762,816

(22) Filed: Apr. 19, 2010

(65) Prior Publication Data

US 2010/0301093 A1 Dec. 2, 2010

Related U.S. Application Data

(62) Division of application No. 11/444,664, filed on Jun. 1, 2006, now Pat. No. 7,722,610.

(60) Provisional application No. 60/686,773, filed on Jun. 2, 2005.

(51) Int. Cl.
*A61B 17/068* (2006.01)

(52) U.S. Cl. .............. 227/175.1; 227/19; 227/176.1; 227/902; 606/61; 606/219; 411/444; 411/474

(58) Field of Classification Search .......... 227/19, 227/176.1, 175.1, 86, 902; 606/61, 139, 606/143, 219; 411/444, 474
See application file for complete search history.

(56) References Cited

U.S. PATENT DOCUMENTS

| | | | |
|---|---|---|---|
| 2,111,404 A | 3/1938 | Pankonin | |
| 2,174,708 A | 10/1939 | Sears et al. | |
| 3,744,495 A | 7/1973 | Johnson | |
| 3,800,653 A | 4/1974 | Barth et al. | |
| 4,047,524 A | 9/1977 | Hall | |
| 4,060,089 A | 11/1977 | Noiles | |
| 4,526,174 A | 7/1985 | Froehlich | |
| 4,534,350 A | 8/1985 | Golden et al. | |
| 4,548,202 A | 10/1985 | Duncan | |
| 4,573,469 A | 3/1986 | Golden et al. | |
| 4,605,001 A | 8/1986 | Rothfuss et al. | |
| 4,608,981 A | 9/1986 | Rothfuss et al. | |
| 4,627,437 A | 12/1986 | Bedi et al. | |
| 4,809,695 A | 3/1989 | Gwathmey et al. | |
| 4,979,954 A | 12/1990 | Gwathmey et al. | |
| 5,007,921 A | 4/1991 | Brown | |
| 5,181,645 A | 1/1993 | Matsutani et al. | |
| 5,258,009 A | 11/1993 | Conners | |
| 5,304,204 A | 4/1994 | Bregen | |
| 5,397,324 A | 3/1995 | Carroll et al. | |
| 5,441,193 A | 8/1995 | Gravener | |
| 5,478,354 A | 12/1995 | Tovey et al. | |
| 5,560,532 A | 10/1996 | DeFonzo et al. | |
| 5,715,987 A | 2/1998 | Kelley et al. | |
| 5,797,931 A | 8/1998 | Bito et al. | |

(Continued)

FOREIGN PATENT DOCUMENTS

GB 1 339 394 12/1973

*Primary Examiner* — Scott A. Smith

(57) ABSTRACT

A multiple coil staple is provided which includes a backspan and a pair of spaced legs. The backspan includes one or more pockets configured to induce coiling of the legs of the staple. A multiple coil staple applier is also provided which includes a pusher having a distal face defining a staple engagement surface and one or more staple deforming pockets. Each staple deforming pocket is configured to induce coiling of the legs of a staple. The multiple coil staple and staple applier facilitate joining of tissues having wider ranges of thicknesses using a single size staple.

9 Claims, 5 Drawing Sheets

U.S. PATENT DOCUMENTS

| | | |
|---|---|---|
| 5,816,471 A | 10/1998 | Plyley et al. |
| 5,817,109 A | 10/1998 | McGarry et al. |
| 5,833,695 A | 11/1998 | Yoon |
| 6,517,556 B1 | 2/2003 | Monassevitch |
| 6,562,051 B1 | 5/2003 | Bolduc et al. |
| 6,638,297 B1 | 10/2003 | Huitema |
| 6,722,552 B2 | 4/2004 | Fenton, Jr. |
| 6,811,555 B1 | 11/2004 | Willis et al. |
| 7,722,610 B2 * | 5/2010 | Viola et al. .............. 606/250 |
| 2002/0026214 A1 | 2/2002 | Tanner et al. |
| 2002/0029048 A1 | 3/2002 | Miller |
| 2003/0139771 A1 | 7/2003 | Fisher et al. |
| 2003/0208211 A1 | 11/2003 | Kortenbach |
| 2004/0199189 A1 | 10/2004 | Gifford, III et al. |
| 2004/0204723 A1 | 10/2004 | Kayan |
| 2004/0249398 A1 | 12/2004 | Ginn |

* cited by examiner

MULTIPLE COIL STAPLE AND STAPLE APPLIER

CROSS REFERENCE TO RELATED APPLICATION

This application is a divisional of application Ser. No. 11/444,664, filed Jun. 1, 2006 now U.S. Pat. No. 7,722,610 which claims the benefit of and priority to U.S. Provisional Patent Application Ser. No. 60/686,773 filed on Jun. 2, 2005. The entire contents of these applications are incorporated by reference herein.

BACKGROUND

1. Technical Field

The present disclosure relates to a fastener and a fastener applier. More particularly, the present disclosure relates to a staple and/or staple applier with structure for curling or coiling staple legs to facilitate joining of tissues having varying thicknesses.

2. Background of Related Art

Surgical staples and stapling instruments are well known in the surgical arts and have become critical to many life saving surgical procedures. The use of stapling instruments for applying staples to join tissue or tissue segments in a fast and efficient manner has obviated the time consuming step of manually suturing tissue or tissue segments in these surgical procedures, e.g., anastomoses procedures. The reduced time required to perform these surgical procedures using surgical stapling instruments has resulted in reduced trauma and risk to patients.

Typically, a surgical staple includes a backspan and a pair of spaced legs. The legs are driven through tissue and into an anvil to deform the staple into a desired configuration, e.g., B-staple, to effect hemostasis of tissue or tissue segments. One problem associated with known staples and staple appliers is that the staples are dimensioned or sized to fasten tissue segments of a given tissue thickness or fasten tissue segments within a predetermined narrow range of thicknesses. Neither the staple nor the staple applier is adapted to deform or reconfigure a staple to facilitate effective hemostatis of tissues having thicknesses outside the predetermined range for a particular size staple.

Accordingly, a continuing need exists in the field of surgery for a surgical staple and/or staple applier which can adapt or reconfigure a surgical staple in a manner which is suitable for use in fastening tissue having a wider range of thicknesses.

SUMMARY

In accordance with the present disclosure, a multiple coil staple is provided which includes a backspan having a top surface and a bottom surface and first and second spaced legs. The first leg extends downwardly from one end of the backspan and the second leg extends downwardly from the other end of the backspan. The bottom surface of the backspan includes one or more pockets positioned to receive the first and second legs of the staple after the first and second legs of the staple have been deformed. The one or more pockets is configured to induce coiling of the first and second legs. In one embodiment, the one or more pockets includes a first pocket positioned to receive the first leg of the staple and a second pocket positioned to receive the second leg of the staple.

The first and second pockets can be configured to induce helical coiling of the first and second legs, respectively. In one embodiment, the first pocket is configured to induce helical coiling in a first direction and the second pocket is configured to induce helical coiling in a second direction opposite to the first direction. The backspan can include an area of increased width to accommodate the one or more pockets.

A multiple coil staple applier is also disclosed which includes a housing defining a staple slot, a staple positioned within the staple slot and having a backspan and a pair of spaced legs, and a pusher dimensioned to be slidably received within the staple slot. The pusher has a distal end having a distal face which defines a staple engagement surface positioned to engage the backspan of the staple and at one or more staple deforming pockets. The one or more staple deforming pockets are configured to induce coiling of the staple legs. In one embodiment, the one or more staple deforming pockets includes first and second staple deforming pockets. The first and second staple deforming pockets can be configured to induce helical coiling of the staple legs. In one embodiment, the first staple deforming pocket is configured to induce helical coiling of the first staple leg in a first direction and the second staple deforming pocket is configured to induce helical coiling of the second staple leg in a second direction opposite the first direction.

The staple engagement surface and the one or more staple deforming pockets can be laterally offset from each other.

In one embodiment, the one or more staple deforming pockets includes first and second staple deforming pockets positioned on one side of the staple engagement surface. In one embodiment, the one or more staple deforming pockets includes first and second staple deforming pockets positioned on opposite sides of the staple engagement surface. Each of the first and second staple deforming pockets can be configured to induce helical coiling of the staple legs.

In one embodiment, the first staple deforming pocket is configured to induce helical coiling of the first staple leg in a first direction and the second staple deforming pocket is configured to induce helical coiling of the second staple leg in a second direction opposite the first direction.

A multiple coil staple is also disclosed which includes a backspan and first and second legs. The backspan has a top surface and a bottom surface wherein the bottom surface has one or more staple deforming pockets. In one embodiment, the one or more staple deforming pockets includes first and second staple deforming pockets. The backspan can includes an area of increased width to accommodate the one or more staple deforming pockets.

A staple pusher for use with a staple applier is also disclosed which includes a body having a distal end having a distal face. The distal face has a staple engagement surface positioned to engage the backspan of a staple and one or more staple deforming pockets configured to induce coiling of legs of a staple. In one embodiment, the one or more staple deforming pockets includes first and second staple deforming pockets.

BRIEF DESCRIPTION OF THE DRAWINGS

Various embodiments of the presently disclosed multiple coil staple are disclosed herein with reference to the drawings, wherein.

DETAILED DESCRIPTION OF EMBODIMENTS

Embodiments of the presently disclosed multiple coil staple and/or staple applier will now be described in detail with reference to the drawings wherein like numerals designate identical or corresponding elements in each of the several views.

Figure 1:
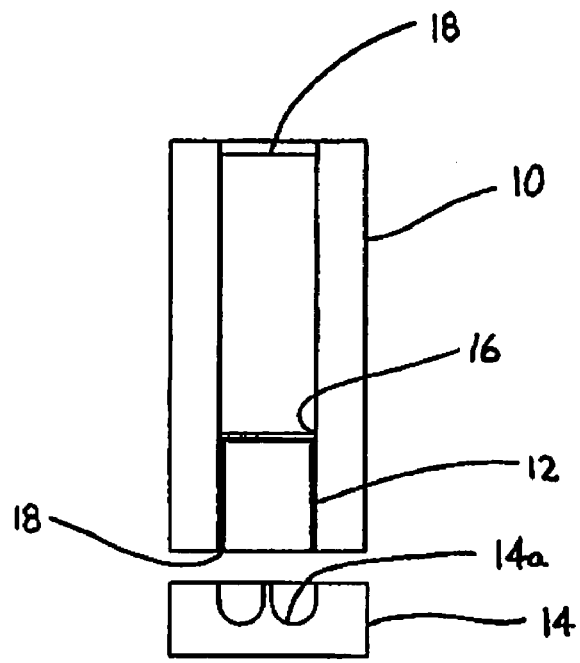
FIG. 1 is a side schematic view of a staple and staple applier.

Referring to FIG. 1, a surgical stapler typically includes a housing 10, one or more staples 12 and an anvil 14 having a staple deforming surface 14a. Housing 10 which may be configured as a cartridge can include at least one staple receiving slot 16 dimensioned to slidably receive a staple 12. In many staplers, a pusher or driver 18 is slidably positioned within slot 16 behind a respective staple 12. An actuator (not shown) is provided to advance pusher 18 through slot 16 and eject staple 12 from an outlet side 20 of cartridge 10 into deforming surface or anvil pocket 14a of anvil 14. Deforming surface 14a can be configured to deform a staple into a desired configuration, e.g., a B-configuration.

Figure 2:
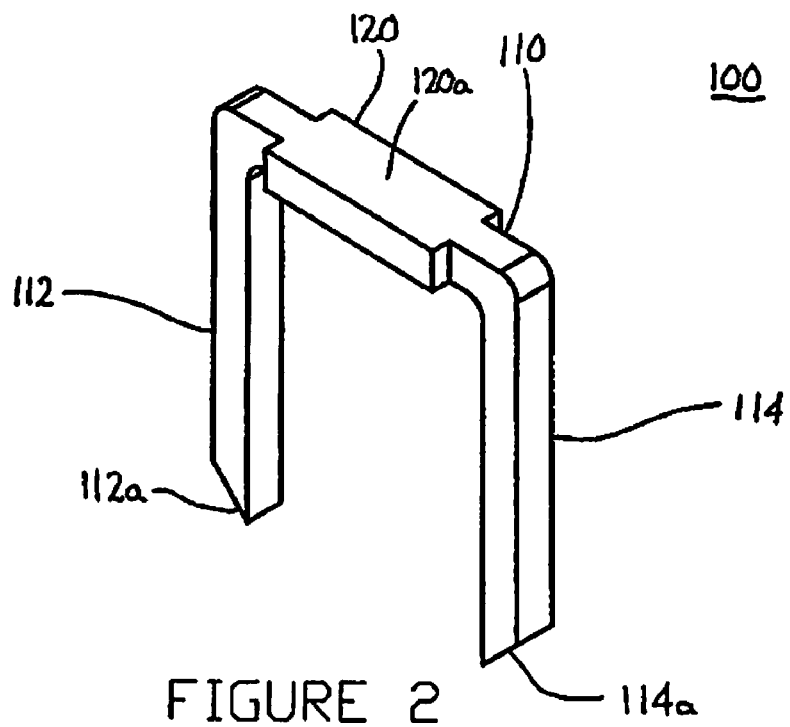
FIG. 2 is a side perspective view of one embodiment of the presently disclosed multiple coil staple.
Figure 3:
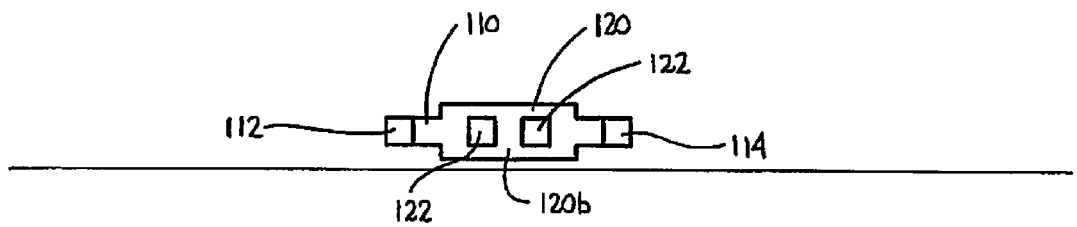
FIG. 3 is a bottom view of the multiple coil staple shown in FIG. 2.
Figure 4:
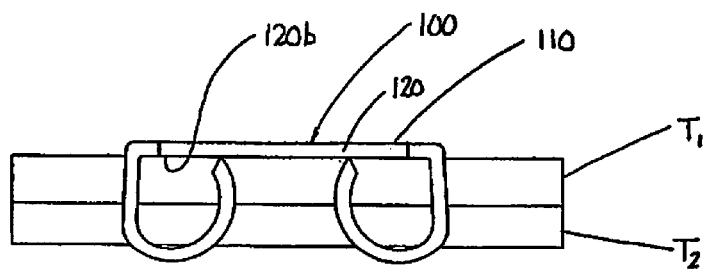
FIG. 4 is a side view of the multiple coil staple shown in FIG. 2 positioned through tissue of relatively large thickness.

Referring to FIGS. 2-4, in one embodiment of the presently disclosed multiple coil staple shown generally as 100, staple 100 includes a backspan 110 and a pair of spaced legs 112 and 114. Legs 112 and 114 each include a tip 112a and 114a. In one embodiment, tips 112a and 114a are tapered or angled inwardly to facilitate tissue penetration. Alternately, other tip configurations to facilitate tissue penetration are envisioned, e.g., conical, tapered outwardly, no taper, etc.

Figure 2A:
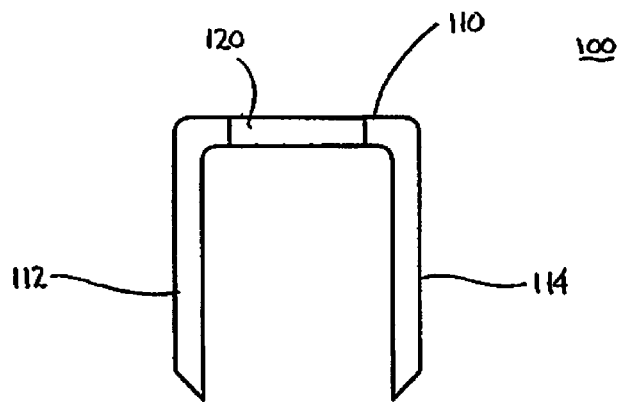
FIG. 2a is a side view of the multiple coil staple shown in FIG. 2.

As illustrated in FIG. 2a, legs 112 and 114 diverge slightly outwardly from each other. Alternately, other staple configurations are envisioned such as where the legs are substantially parallel or converge inwardly. Legs 112 and 114 can have a substantially rectangular cross-sectional shape. It is also envisioned that the cross-sectional shape of legs 112 and 114 can include other configurations including oval, circular, square, triangular, trapezoidal, etc. The staple may also be configured as a directionally biased staple such as that described in U.S. patent application Ser. No. 09/972,594 filed Nov. 5, 2001, which is incorporated herein in its entirety by reference.

Referring to FIGS. 2-3, in one embodiment, backspan 110 includes a widened portion or area of increased width 120, i.e., a width greater than the remaining portion of backspan 110, having a top surface 120a and a bottom surface 120b. Bottom surface 120b includes one or more forming buckets or pockets 122 (FIG. 3). As used herein, the term forming pocket means any depression, recess, bucket, groove or the like configured to receive one or both staple legs to effect deformation of the staple legs. Forming pockets 122 are positioned and configured on backspan 110 to engage tips 112a and 114a of staple 100 during formation of staple 100 to induce curling or coiling of legs 112 and 114. It is envisioned that pockets 122 may be eliminated such that the leg tips engage the substantially flat bottom surface of backspan 110. Further, backspan 110 need not have a widened portion. Alternatively, forming pockets can be formed in the bottom surface of a normal sized backspan of a staple.

Figure 5:
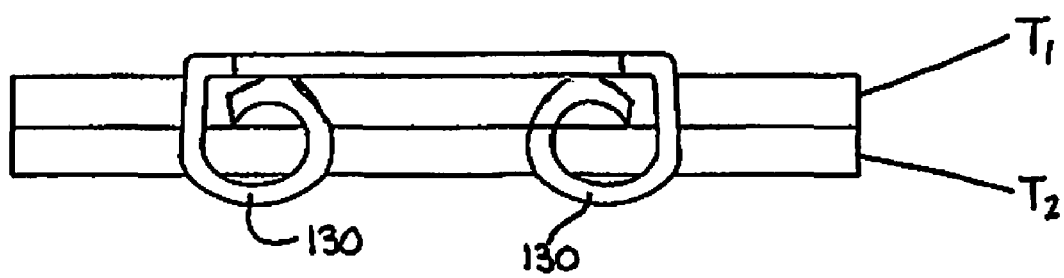
FIG. 5 is a side view of the multiple coil staple shown in FIG. 2 positioned through tissue of relatively moderate thickness.

Referring to FIG. 4, when staple 100 is fired from a stapling instrument (not shown) through relatively thick tissue, legs 112 and 114 pass through tissue segments $T_1$ and $T_2$ and are curled upwardly by an anvil (see FIG. 1) of the stapling instrument towards bottom surface 120b of backspan 110. As illustrated in FIG. 4, because the tissue segments $T_1$ and $T_2$ are relatively thick, tissue segments $T_1$ and $T_2$ are approximated and hemostasis is effected by the time tips 112a and 114a engage or approach forming pockets 122. However, as illustrated in FIG. 5, where tissue segments $T_1$ and $T_2$ are of moderate thickness, tips 112a and 114a engage pockets 122 during staple formation. Pockets 122 redirect or coil legs 112 and 114 downwardly. As a result, legs 112 and 114 are coiled, thus allowing backspan 110 to approach a tissue holding portion 130 of each of legs 112 and 114 to maintain approximation and effect hemostasis of tissue segments $T_1$ and $T_2$. As used herein, the term "tissue holding portion" refers to the portion of the staple legs which engages an outer surface of the tissue or tissue section opposite the backspan of the staple as the staple is deformed.

Figure 6:
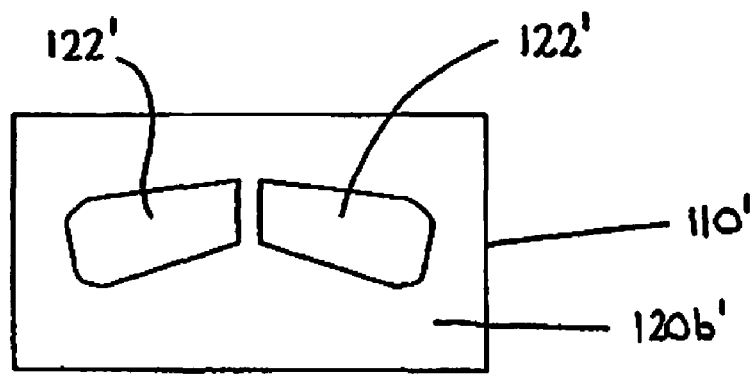
FIG. 6 is an enlarged bottom view of the staple pockets of another embodiment of the multiple coil staple.

The configuration of pocket or pockets 122 can be modified to control the direction and/or shape of staple leg coiling. For example, as illustrated in FIG. 6, the pitch or angle of the deforming surface of the one or more pockets 122' on bottom surface 120b' of backspan 110' can be changed to effect helical curling or coiling of legs 112 and 114 of staple 110. Other pocket configurations are envisioned to effect different types of staple leg deformation, e.g., the pitch of adjacent pockets 122 can be reversed to effect helical coiling of legs 112 and 114 in opposite directions.

Figure 8:
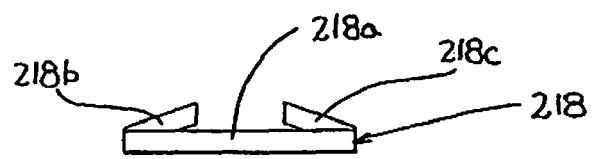
FIG. 8 is a top view of a staple deformed by the multiple coil staple applier shown in FIG. 7.

FIG. 8 illustrates one embodiment of the presently disclosed pusher of a multiple coil staple applier (FIG. 1). In this embodiment, the location of the staple pockets has been moved from the staple to the staple pusher as will be described in detail below. As discussed with respect to FIG. 1 above, a staple applier typically includes a housing 10 defining a staple channel or slot 16, a pusher 18 and an anvil 14. In the presently disclosed staple applier, a pusher 214 is provided to drive a staple 218. Housing 10 can be configured as a cartridge housing to support one or more staples 218 or housing 10 can be configured as the portion of a surgical stapler which defines an ejection port for a surgical staple 218. Pusher 214 can be configured as the pushing element associated with a staple in a staple cartridge or the drive member of a surgical stapler.

Figure 7:
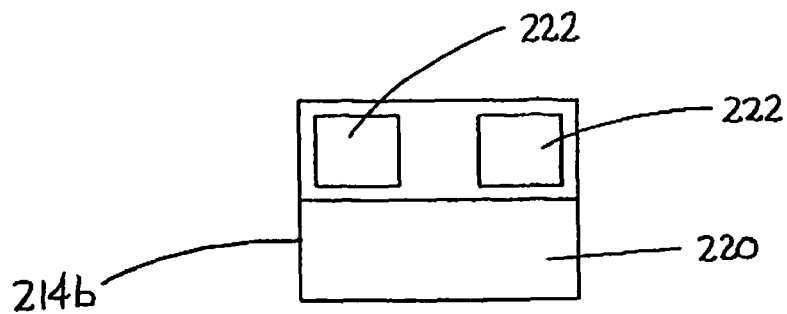
FIG. 7 is a bottom view of the distal end of the pusher of one embodiment of the presently disclosed multiple coil staple applier.

Pusher 214 includes a proximal end 214a and a distal end 214b. Proximal end 214a is operably associated with the drive member (not shown) of a surgical stapler. The drive member is actuable to advance pusher 214 along channel 16 (FIG. 1) to drive a staple 218 from housing 10 into staple pockets 14a of anvil 14. Distal end 214b of pusher 214 has a distal face defining a staple engagement surface 220 (FIG. 7) and one or more pockets 222 configured to redirect staple legs 218b and 218c downwardly in a particular or desired direction. Staple engagement surface 220 can be configured to engage the backspan 218a of staple 218, e.g., engagement surface 220 can include a concavity (not shown) for receiving a portion of backspan 218a of staple 218. In one embodiment, two pusher pockets 222 are provided on the distal face of distal end 214b of pusher 214. Pockets 222 are both laterally offset to one side of engagement surface 220.

In use, when pusher 214 is advanced within channel 16 (FIG. 1), staple 218 is pushed from channel 16 by pusher 214 such that legs 218b and 218c of staple 218 enter and are deflected upwardly and laterally by anvil pockets 14a. As legs 218b and 218c of staple 218 move upwardly, legs 218b and 218c enter pockets 222 of pusher 214 to deflect or curl legs downwardly back towards anvil 14. The combined effect of anvil pockets 14 and pusher pockets 222 curls or spirals staple legs 218b and 218c laterally of engagement surface 220 (see FIG. 9).

Figure 9:
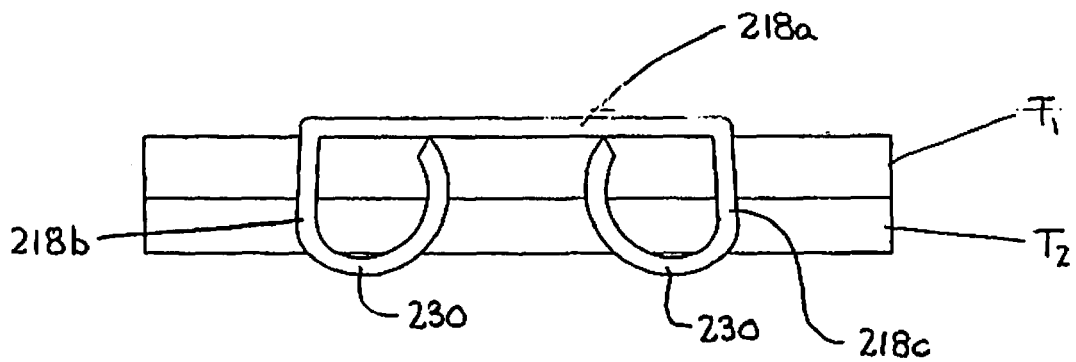
FIG. 9 is a side view of the staple shown in FIG. 8 positioned in tissue having a relatively large thickness.
Figure 9A:
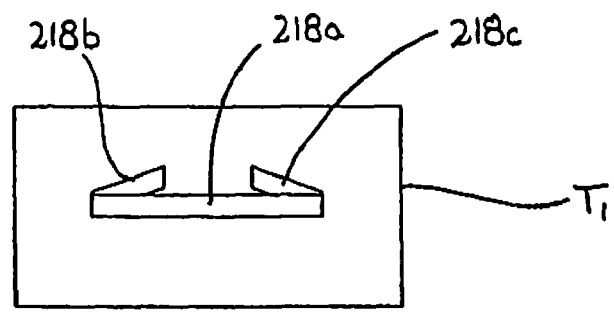
FIG. 9a is a top view of the deformed staple shown in FIG. 9.
Figure 10:
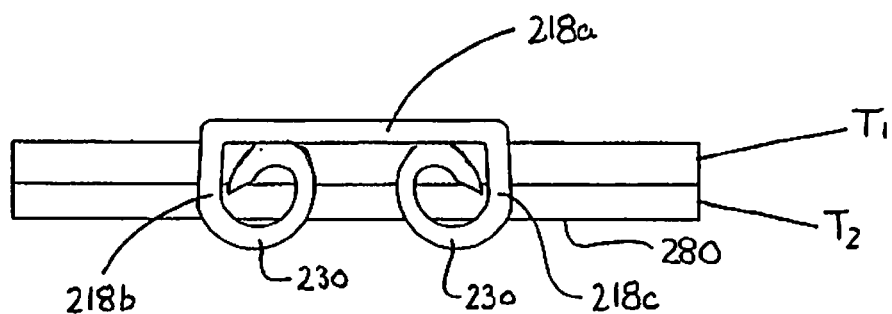
FIG. 10 is a side view of the staple shown in FIG. 8 positioned in tissue having a relatively moderate thickness.

Referring to FIGS. 9, and 10, a staple applier including pusher 218 can be used to fasten tissue sections $T_1$ and $T_2$ having relatively large thicknesses (FIG. 9) as well as tissue sections $T_1$ and $T_2$ having relatively small tissue thicknesses (FIG. 10). This is so because by curling legs 218b and 218c of staple 218, backspan 218a of staple 218 is able to approach tissue holding portions 230, of staple 218. That is, since tissue sections $T_1$ and $T_2$ are compressed between backspan 218a and holding portions 230 of the staple legs, and curling the staple legs changes the distance between backspan 218a and holding portions 230, varying tissue thicknesses can be fastened using a single size staple by curling the staple legs.

Figures 11, 12:
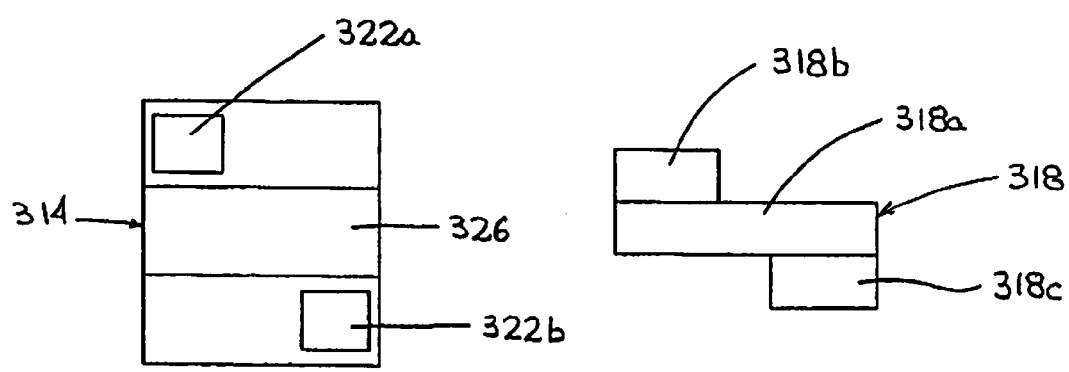
FIG. 11 is a bottom view of the distal end of the pusher of another embodiment of the presently disclosed multiple coil staple applier.
FIG. 12 is a top view of a staple deformed by the multiple coil staple applier shown in FIG. 11.

FIGS. 11 and 12 illustrate an alternate embodiment of the pusher of the multiple coil staple applier shown in FIGS. 7-10. As shown in FIGS. 11 and 12, distal end 314b of pusher 314 includes an engagement surface 326, a first staple pocket 322a laterally offset to one side of engagement surface 326 and a second staple pocket 322b which is laterally offset to the other side of engagement surface 326. Anvil pockets 14a of anvil 14 (FIG. 1) are configured to deflect staple leg 318b of staple 318 upwardly and laterally towards first staple pocket 322a and deflect staple leg 318c of staple 318 upwardly and towards second staple pocket 322b. Pockets 322a and 322b of pusher 314 are positioned to receive staple legs 318b and 318c of staple 318 to curl leg 318b to one side of backspan 318a, and curl leg 318c to the other side of backspan 318a such as shown in FIG. 12.

The presently disclosed multiple coil staple and/or staple applier may be incorporated into known surgical stapling instruments including both open and endoscopic instruments and sequential, single, and multiple fire instruments. Examples of such instruments are disclosed in the following U.S. Patents which are incorporated into this application in their entirety by reference: U.S. Pat. Nos. 6,045,560, 5,964,394, 5,894,979, 5,878,937, 5,915,616, 5,836,503, 5,865,361, 5,862,972, 5,817,109, 5,797,538 and 5,782,396. It is also envisioned that the presently disclosed embodiments of the multiple coil staple and/or staple applier could also be incorporated into robotically operated surgical staplers.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A multiple coil staple applier comprising:
a housing defining a staple slot;
a staple positioned within the staple slot and having a backspan and a pair of spaced legs;
a pusher dimensioned to be slidably received within the staple slot, the pusher having a distal end having a distal face, the distal face defining a staple engagement surface positioned to engage the backspan of the staple and one or more staple deforming pockets, the one or more staple deforming pockets being configured to induce coiling of the staple legs.

2. A multiple coil staple applier according to claim 1, wherein the one or more staple deforming pockets includes first and second staple deforming pockets.

3. A multiple coil staple applier according to claim 2, wherein the first and second staple deforming pockets are configured to induce helical coiling of the staple legs.

4. The multiple coil staple applier of claim 1, wherein a first staple deforming pocket is configured to induce helical coiling of a first staple leg in a first direction and a second staple deforming pocket is configured to induce helical coiling of a second staple leg in a second direction opposite the first direction.

5. A multiple coil staple applier according to claim 1, wherein the staple engagement surface and the one or more staple deforming pockets are laterally offset from each other.

6. A multiple coil staple applier according to claim 5, wherein the one or more staple deforming pockets includes first and second staple deforming pockets positioned on one side of the staple engagement surface.

7. A multiple coil staple applier according to claim 5, wherein the one or more staple deforming pockets includes first and second staple deforming pockets positioned on opposite sides of the staple engagement surface.

8. A multiple coil staple applier according to claim 7, wherein each of the first and second staple deforming pockets is configured to induce helical coiling of the staple legs.

9. A multiple coil staple applier according to claim 8, wherein the first staple deforming pocket is configured to induce helical coiling of the first staple leg in a first direction and the second staple deforming pocket is configured to induce helical coiling of the second staple leg in a second direction opposite the first direction.

* * * * *